(12) United States Patent  
Higashiyama et al.

(10) Patent No.: US 10,982,679 B2
(45) Date of Patent: Apr. 20, 2021

(54) BLOWING APPARATUS

(71) Applicant: Murata Manufacturing Co., Ltd., Kyoto (JP)

(72) Inventors: Yuzo Higashiyama, Kyoto (JP); Shigeru Tsuji, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 265 days.

(21) Appl. No.: 15/898,761

(22) Filed: Feb. 19, 2018

(65) Prior Publication Data
US 2018/0169359 A1 Jun. 21, 2018

Related U.S. Application Data

(63) Continuation of application No. PCT/JP2016/071791, filed on Jul. 26, 2016.

(30) Foreign Application Priority Data

Aug. 18, 2015 (JP) .............................. JP2015-161199

(51) Int. Cl.
*F04D 25/06* (2006.01)
*F04D 29/42* (2006.01)
(Continued)

(52) U.S. Cl.
CPC ........... *F04D 25/068* (2013.01); *F04D 17/16* (2013.01); *F04D 27/001* (2013.01);
(Continued)

(58) Field of Classification Search
CPC .... F04D 25/068; F04D 27/004; F04D 29/663; F04D 27/001; F04D 17/16;
(Continued)

(56) References Cited

U.S. PATENT DOCUMENTS 4,773,829 A * 9/1988 Vettori .................... H02K 7/14
310/68 R
5,515,444 A * 5/1996 Burdisso .............. G10K 11/178
381/71.5
(Continued)

FOREIGN PATENT DOCUMENTS

CN 102243869 A 11/2011
CN 203488400 U 3/2014
(Continued)

OTHER PUBLICATIONS

Notice of Reason for Rejection for Japanese Patent Application No. 2017-535305 dated Feb. 12, 2019.
(Continued)

*Primary Examiner* — Charles G Freay
(74) *Attorney, Agent, or Firm* — Pearne & Gordon LLP

(57) ABSTRACT

A blowing apparatus includes a blowing unit, a first circuit board, a second circuit board, a top casing, a middle casing, and a bottom casing. The bottom casing has an intake hole. The middle casing has a nozzle to which a tube is attached, and also has an exhaust hole inside the nozzle. The exhaust hole is connected to a mask, with the tube interposed therebetween. The blowing unit includes a fan and a motor configured to rotate the fan. The blowing unit is located in a region between the first circuit board and the second circuit board. The first circuit board intersects a rotation axis of the fan. The first circuit board covers the blowing unit as viewed from the top casing in plan view of the first circuit board.

13 Claims, 9 Drawing Sheets

(51) Int. Cl.
*F04D 17/16* (2006.01)
*F04D 27/00* (2006.01)
*F04D 29/66* (2006.01)
*A61M 16/00* (2006.01)
*A61M 16/08* (2006.01)
*A61M 16/10* (2006.01)

(52) U.S. Cl.
CPC ....... *F04D 27/004* (2013.01); *F04D 29/4226* (2013.01); *F04D 29/663* (2013.01); *A61M 16/0066* (2013.01); *A61M 16/0069* (2014.02); *A61M 16/024* (2017.08); *A61M 16/0875* (2013.01); *A61M 16/105* (2013.01); *A61M 2016/0027* (2013.01); *A61M 2205/3365* (2013.01); *A61M 2205/3375* (2013.01); *A61M 2205/42* (2013.01); *F05D 2270/334* (2013.01)

(58) Field of Classification Search
CPC .............. F04D 29/4226; F04D 25/086; A61M 16/024; A61M 16/105; A61M 16/0066; A61M 16/0875; A61M 16/0069; A61M 2016/0027; A61M 2205/3365; A61M 2205/3375; F05D 2270/334
See application file for complete search history.

(56) References Cited

U.S. PATENT DOCUMENTS

| | | | | | |
|---|---|---|---|---|---|
| 5,638,311 | A * | 6/1997 | Fujii | .................... | G10K 11/178 708/322 |
| 5,828,760 | A * | 10/1998 | Jacobson | ......... | G10K 11/17875 381/71.11 |
| 5,995,632 | A | 11/1999 | Okada | | |
| 6,188,770 | B1 | 2/2001 | Okada | | |
| 6,737,824 | B1 * | 5/2004 | Aslan | .............. | F04D 27/004 318/445 |
| 7,617,823 | B2 * | 11/2009 | DiMatteo | .......... | A61M 16/0066 128/204.18 |
| 8,453,640 | B2 * | 6/2013 | Martin | ................. | A61M 16/06 128/203.17 |
| 2007/0247009 | A1 * | 10/2007 | Hoffman | ................. | H02K 7/14 310/51 |
| 2011/0017212 | A1 | 1/2011 | Kenyon et al. | | |
| 2011/0163861 | A1 | 7/2011 | Uetake | | |
| 2011/0255704 | A1 * | 10/2011 | Hopkins | ............... | F04D 29/665 381/71.3 |
| 2012/0199129 | A1 * | 8/2012 | Kenyon | .................. | F04D 17/16 128/205.25 |
| 2014/0010682 | A1 | 1/2014 | Suzuki et al. | | |
| 2014/0166007 | A1 | 6/2014 | Bordewick et al. | | |
| 2014/0207218 | A1 | 7/2014 | Pierre et al. | | |
| 2015/0335921 | A1 * | 11/2015 | Hagen | .................. | A62B 18/006 128/204.21 |
| 2016/0022954 | A1 * | 1/2016 | Bath | .................... | A61M 16/16 128/203.27 |

FOREIGN PATENT DOCUMENTS

| | | |
|---|---|---|
| JP | H03-111700 A | 5/1991 |
| JP | H07-275632 A | 10/1995 |
| JP | H10-20866 A | 1/1998 |
| JP | 2004-117586 A | 4/2004 |
| JP | 2006-002651 A | 1/2006 |
| JP | 2006-323176 A | 11/2006 |
| JP | 2007-064082 A | 3/2007 |
| JP | 2008-518640 A | 6/2008 |
| JP | 2009-533153 A | 9/2009 |
| JP | 2011-141667 A | 7/2011 |
| JP | 2011-227502 A | 11/2011 |
| JP | 2011-249380 A | 12/2011 |
| JP | 2014-15849 A | 1/2014 |
| JP | 2014-60064 A | 4/2014 |
| WO | 2012-017478 A1 | 2/2012 |

OTHER PUBLICATIONS

Chinese Office Action for Chinese Application No. 201680048199.2 dated Mar. 4, 2019.
International Search Report for International Application No. PCT/JP2016/071791, dated Oct. 18, 2016.
Written Opinion for International Application No. PCT/JP2016/071791, dated Oct. 18, 2016.
Office Action for Chinese Patent Application No. 201680048199.2 dated Oct. 10, 2020.
"Noise Control Engineering" (translated from Chinese), Chief Editor: Qiang Gu, published on Aug. 31, 2002, Coal Industry Publishing House, pp. 91-101. [Concise Statement of Relevance Included in English Translation of Chinese Office Action dated Oct. 10, 2020].

* cited by examiner

BLOWING APPARATUS

This is a continuation of International Application No. PCT/JP2016/071791 filed on Jul. 26, 2016 which claims priority from Japanese Patent Application No. 2015-161199 filed on Aug. 18, 2015. The contents of these applications are incorporated herein by reference in their entireties.

BACKGROUND OF THE DISCLOSURE

Field of the Disclosure

The present disclosure relates to a blowing apparatus that blows a gas.

Description of the Related Art

As a treatment for sleep apnea syndrome, continuous positive airway pressure (CPAP) has been conventionally performed, which applies a constant pressure to the airway of the patient by sending air thereinto through a mask worn over the nose of the patient. The continuous positive airway pressure (CPAP) uses a blowing apparatus that blows air.

For example, Patent Document 1 discloses a blowing apparatus that includes a blower (blowing unit). The blower includes a fan and a motor that rotates the fan. For example, while the patient is sleeping, the blowing apparatus drives the motor to rotate the fan. The blowing apparatus thus sends air from the fan to a mask, and keeps pressure in the airway of the patient at a constant level. While the motor is being driven, the blower produces noise and vibration.

In the blowing apparatus disclosed in Patent Document 1, the blower is covered with an enclosure, and the enclosure is covered with a case. The enclosure is made of a composite material of metal and polymer. The case is made of a resin. The blowing apparatus disclosed in Patent Document 1 thus prevents the noise and vibration produced by the blower from leaking to the outside of the case.

Patent Document 1: Japanese Unexamined Patent Application Publication (Translation of PCT Application) No. 2008-518640

BRIEF SUMMARY OF THE DISCLOSURE

Covering the blower (blowing unit) with multiple layers increases the weight of the blowing apparatus. This makes it difficult for the user to move or carry the blowing apparatus disclosed in Patent Document 1.

An object of the present disclosure is to provide a blowing apparatus that is capable of significantly attenuating the noise and vibration produced by a blowing unit without a significant increase in weight.

A blowing apparatus according to the present disclosure includes a blowing unit, a first circuit board, and a casing. The blowing unit includes a fan and a motor configured to rotate the fan. The first circuit board has a control circuit mounted thereon, and intersects a rotation axis of the fan. The control circuit is configured to control drive of the motor. The casing has an intake hole and an exhaust hole, and houses the blowing unit and the first circuit board. The first circuit board overlaps with the blowing unit in a plan view of the first circuit board.

In this configuration, the blowing unit produces noise and vibration while the motor is being driven. The fan includes a plurality of blades extending radially with respect to the rotation axis. The diameter of the fan is greater than the thickness of the fan. That is, the area of the upper surface of the fan is greater than the area of the side face of the fan.

In this configuration, the first circuit board intersects the rotation axis of the fan and covers at least part of the blowing unit. That is, in this configuration, the side face of the blowing unit is covered with the casing (single layer), and the upper surface of the blowing unit is covered with the first circuit board and the casing (multiple layers). Therefore, the blowing apparatus with this configuration can significantly attenuate the noise and vibration transmitted from the upper surface of the blowing unit having a large area. At the same time, the blowing apparatus with this configuration is lightweight, because the side face of the blowing unit having a small area is not covered with multiple layers.

The blowing apparatus with this configuration can thus significantly attenuate the noise and vibration produced by the blowing unit without a significant increase in weight.

The blowing apparatus according to the present disclosure preferably further includes a second circuit board intersecting the rotation axis of the fan and housed in the casing. The blowing unit is preferably located in a region between the first circuit board and the second circuit board.

In this configuration, the lower surface of the blowing unit is also covered with multiple layers, the second circuit board and the casing. This enables the blowing apparatus with this configuration to significantly attenuate the noise and vibration transmitted from the lower surface of the blowing unit having a large area.

In the blowing apparatus according to the present disclosure, the casing preferably has a securing portion configured to secure the first circuit board. The first circuit board and the securing portion are preferably bonded together with an elastic member interposed therebetween.

With the elastic member, the blowing apparatus with this configuration can block the noise from leaking through the gap between the first circuit board and the securing portion.

In the blowing apparatus according to the present disclosure, the control circuit preferably includes a filter circuit configured to attenuate signals in a specific band.

The blowing apparatus with this configuration can thus suppress the noise and vibration produced by the blowing unit.

The blowing apparatus according to the present disclosure preferably further includes a sensor configured to detect a frequency of sound or vibration produced by driving the motor. The control circuit preferably makes setting of the filter circuit in accordance with a detection result outputted by the sensor.

The blowing apparatus with this configuration can identify the frequency of the noise or vibration produced by the blowing unit and set the identified frequency in the filter circuit.

The blowing apparatus according to the present disclosure preferably further includes a microphone configured to detect a first sound produced by the blowing unit, and a sound absorbing speaker configured to produce a second sound having a phase opposite to that of the first sound detected by the microphone. The sound absorbing speaker is preferably housed in the casing while facing toward the intake hole.

The blowing apparatus with this configuration can cancel out the noise leaking through the intake hole.

In the blowing apparatus according to the present disclosure, the fan preferably includes a plurality of blades extending radially with respect to the rotation axis. The exhaust hole is preferably located outside a perimeter of the plurality of blades with respect to the rotation axis. A diameter of the exhaust hole is preferably greater than a length of the blades in a direction parallel to the rotation axis.

With this configuration, a gas discharged from the fan easily reaches the exhaust hole directly without hitting other components. The blowing apparatus with this configuration can thus efficiently discharge the gas from the fan through the exhaust hole. Since the gas is less likely to hit other components, the blowing apparatus with this configuration can achieve a silencing effect.

The blowing apparatus according to the present disclosure is capable of significantly attenuating the noise and vibration produced by the blowing unit without a significant increase in weight.

DETAILED DESCRIPTION OF THE DISCLOSURE

A blowing apparatus according to embodiments of the present disclosure will now be described.

Figure 1:
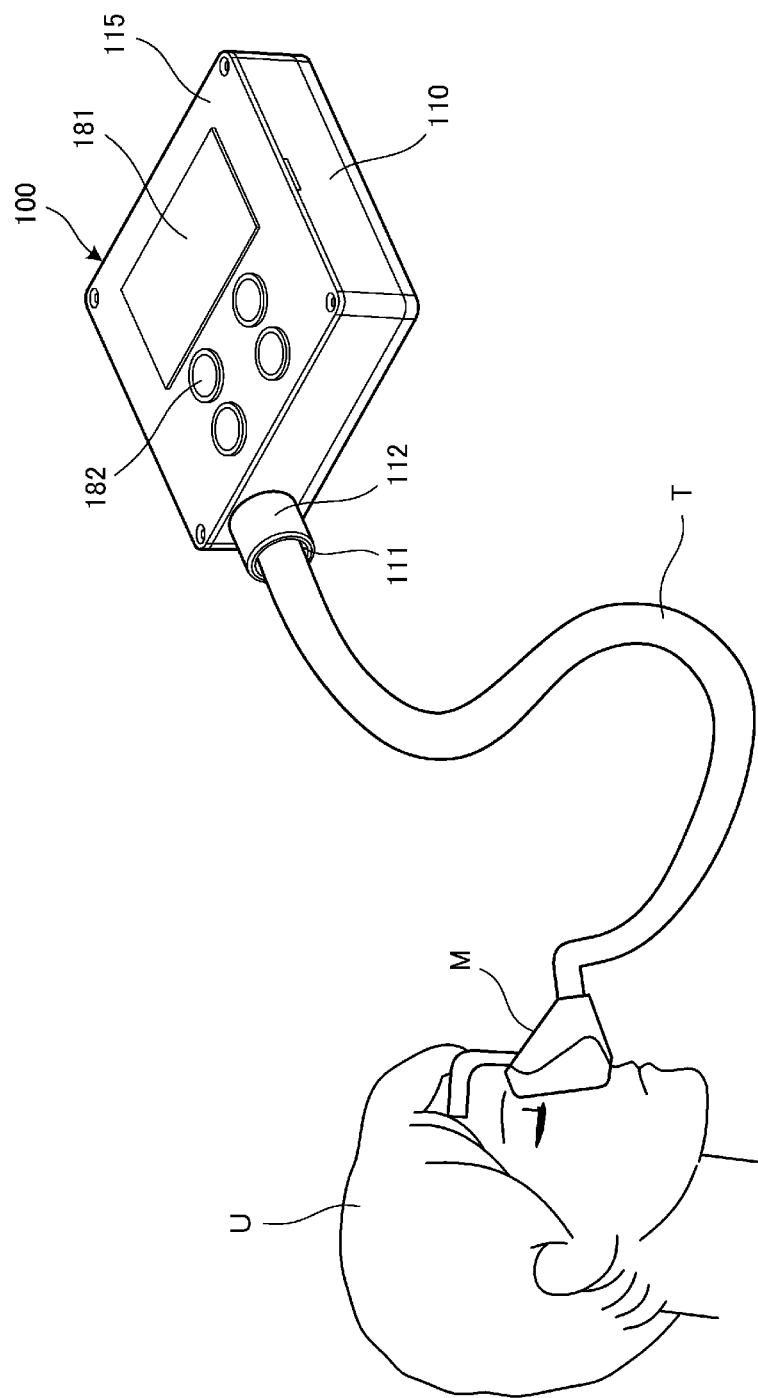
FIG. 1 is an external perspective view of a blowing apparatus 100 according to an embodiment of the present disclosure.
Figure 2:
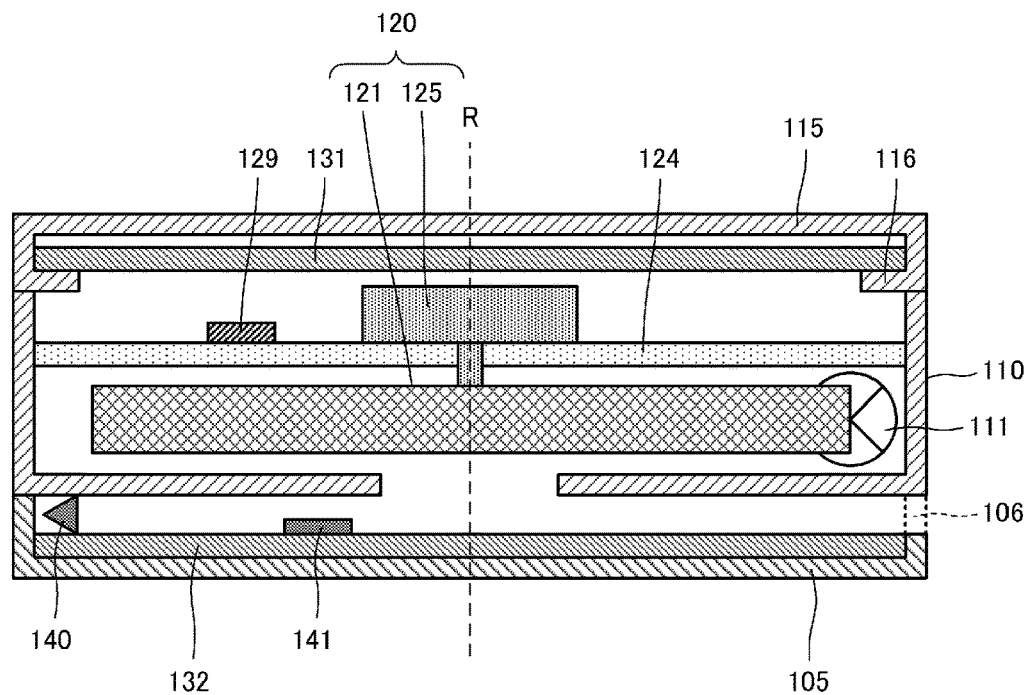
FIG. 2 is a cross-sectional view of a main part of the blowing apparatus 100 illustrated in FIG. 1.
Figure 3:
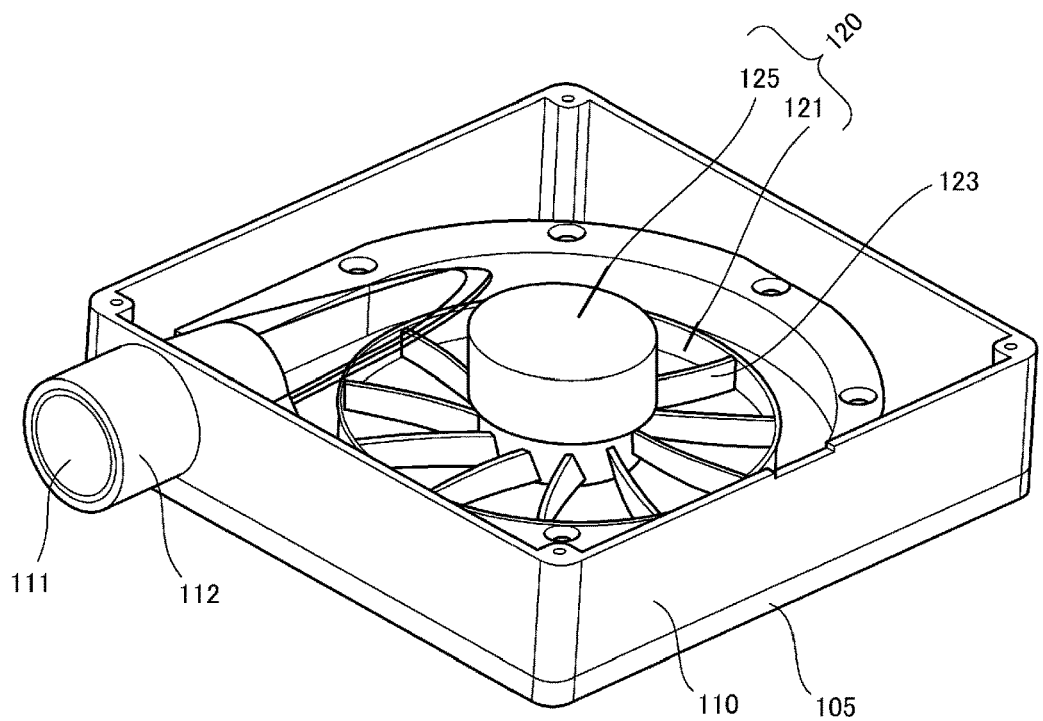
FIG. 3 is an external perspective view of an interior of the blowing apparatus 100 illustrated in FIG. 1.

FIG. 1 is an external perspective view of a blowing apparatus 100 according to an embodiment of the present disclosure. FIG. 2 is a cross-sectional view of a main part of the blowing apparatus 100 illustrated in FIG. 1. FIG. 3 is an external perspective view of an interior of the blowing apparatus 100, with a top casing 115 and a first circuit board 131 removed from a middle casing 110.

The blowing apparatus 100 includes a blowing unit 120, the first circuit board 131, a second circuit board 132, a sensor 129, a microphone 141, a sound absorbing speaker 140, a tube T, a mask M, the top casing 115, the middle casing 110, and a bottom casing 105. The blowing apparatus 100 is used for continuous positive airway pressure (CPAP), which is a treatment for sleep apnea syndrome.

Note that the top casing 115, the middle casing 110, and the bottom casing 105 correspond to a casing of the present disclosure.

The top casing 115, the middle casing 110, and the bottom casing 105 are joined together to form a single casing. The bottom casing 105 has an intake hole 106. The middle casing 110 has a nozzle 112 to which the tube T is attached, and also has an exhaust hole 111 inside the nozzle 112. As illustrated in FIG. 1, the exhaust hole 111 is connected to the mask M, with the tube T interposed therebetween.

The top casing 115, the middle casing 110, and the bottom casing 105 are configured to house the blowing unit 120, the first circuit board 131, the second circuit board 132, the sensor 129, the microphone 141, and the sound absorbing speaker 140.

The top casing 115 has a securing portion 116 protruding toward the inside of the top casing 115. The first circuit board 131 is placed on the securing portion 116, and is bonded to the securing portion 116 with an elastic member (e.g., rubber member) interposed therebetween. With the elastic member, the blowing apparatus 100 can block the noise of the blowing unit 120 from leaking through the gap between the first circuit board 131 and the securing portion 116.

The middle casing 110 has a mounting plate 124. The mounting plate 124 is made of a vibration absorbing material, such as elastomer or sheet steel. The blowing unit 120 and the sensor 129 are mounted on the mounting plate 124.

The sensor 129 is, for example, an acceleration sensor. The sensor 129 detects the frequency of sound or vibration produced by the blowing unit 120. The second circuit board 132 is placed on the bottom casing 105, and is bonded to the bottom casing 105 with an elastic member (e.g., rubber member) interposed therebetween.

The blowing unit 120 includes a fan 121 and a motor 125 configured to rotate the fan 121. The fan 121 includes a plurality of blades 123 that extend radially with respect to a rotation axis R. As illustrated in FIGS. 2 and 3, the exhaust hole 111 is located outside the perimeter of the plurality of blades 123 with respect to the rotation axis R. The diameter of the exhaust hole 111 is greater than the length of the blades 123 in a direction parallel to the rotation axis. The blowing unit 120 is located in a region between the first circuit board 131 and the second circuit board 132.

The first circuit board 131 is a multilayer substrate composed of a plurality of layers. The first circuit board 131 perpendicularly intersects the rotation axis R of the fan 121. The first circuit board 131 covers the blowing unit 120 as viewed from the top casing 115 in a plan view of the first circuit board 131.

The second circuit board 132 is a multilayer substrate composed of a plurality of layers. The second circuit board 132 perpendicularly intersects the rotation axis R of the fan 121. The second circuit board 132 covers the blowing unit 120 as viewed from the bottom casing 105 in a plan view of the second circuit board 132.

With the configuration described above, for example as illustrated in FIG. 1, the blowing apparatus 100 drives the motor 125 to rotate the fan 121 while a patient U is sleeping. Air is sucked in through the intake hole 106 by rotation of the fan 121, and flows in from below the fan 121. Then, from the perimeter of the fan 121, the air is discharged radially with respect to the rotation axis R toward the exhaust hole 111.

The air discharged from the exhaust hole 111 passes through the tube T and flows into the mask M worn over the nose of the patient U. The air in the mask M flows through the mouth or nose into the airway of the patient U. This enables the blowing apparatus 100 to apply a constant pressure (e.g., ranging from 4 cm $H_2O$ to 20 cm $H_2O$) to the airway of the patient U. The blowing apparatus 100 thus prevents the airway of the patient U from being obstructed during sleep, and prevents the patient U from stopping breathing.

To apply a constant pressure to the airway of the patient U, the blowing apparatus 100 needs to rotate the motor 125 at a high speed. This increases the reaction torque of the motor 125. As a result, the reaction torque excites the resonant frequency of the blowing unit 120 and makes the blowing unit 120 prone to vibration. Also, the fan 121 may produce a vibration sound or noise, such as large wind noise, at a frequency corresponding to "(the rotation speed of the fan 121)×(the number of blades)" and an integral multiple of this frequency.

This means that while the motor 125 is being driven, the blowing unit 120 may produce noise or vibration while the patient U is sleeping.

Figure 4:
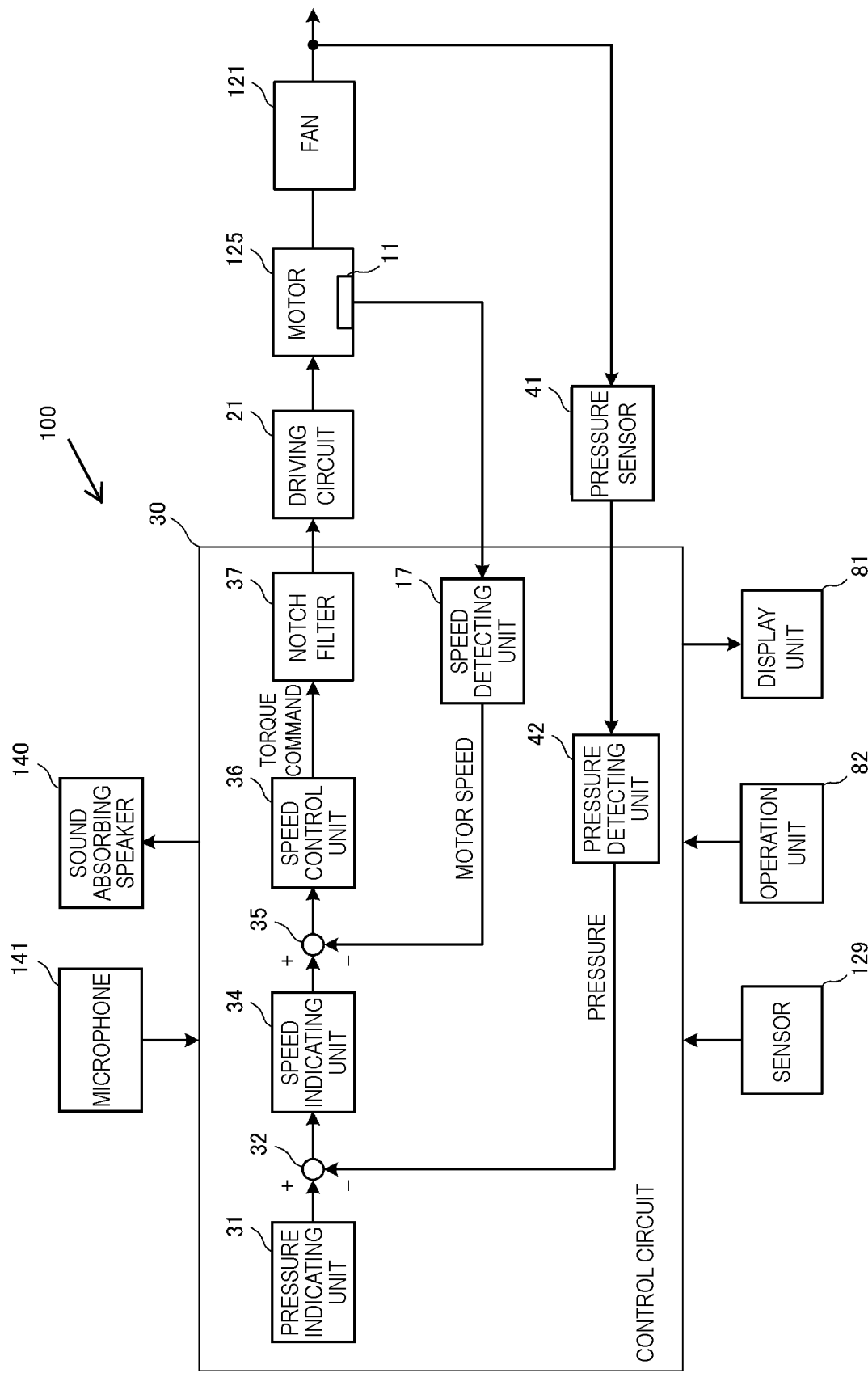
FIG. 4 is a block diagram of the blowing apparatus 100 illustrated in FIG. 1.
Figure 5:
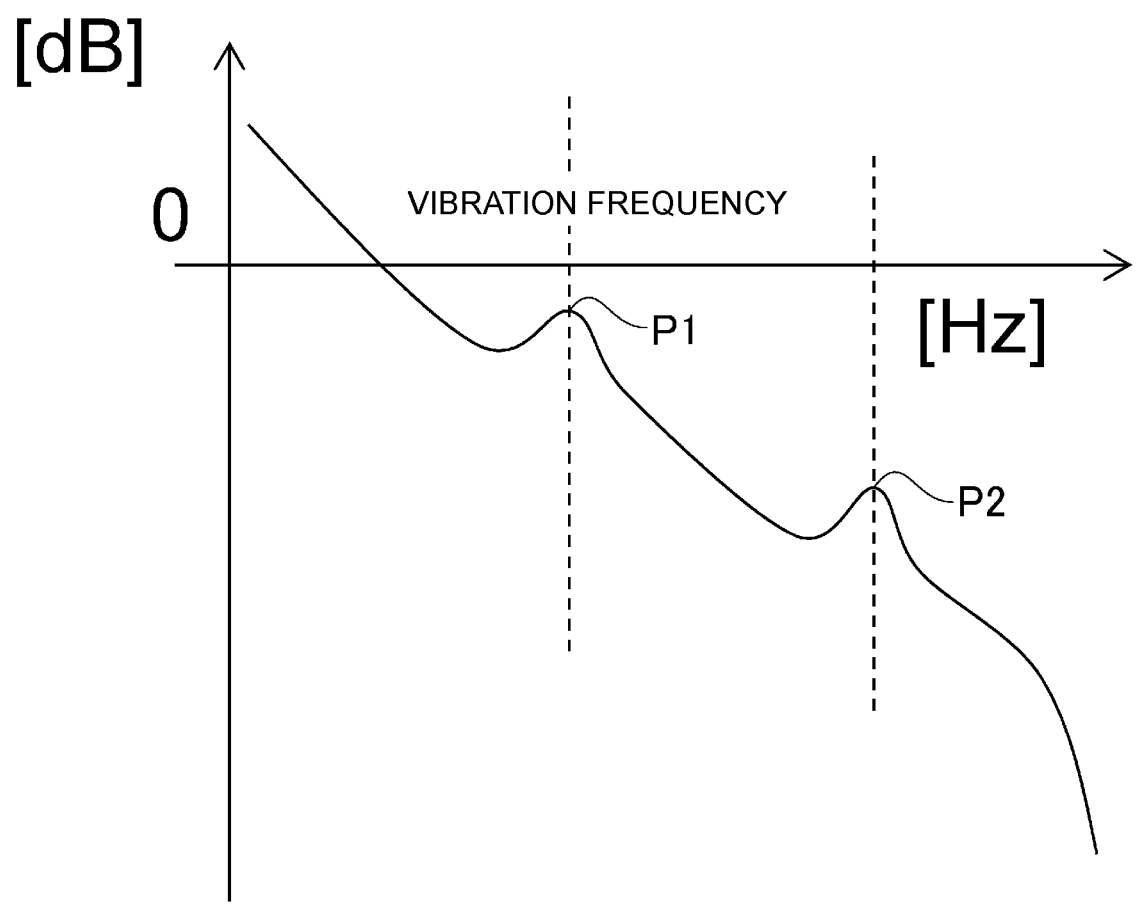
FIG. 5 shows a vibration frequency response curve of a control system loop without a notch filter 37.
Figure 6:
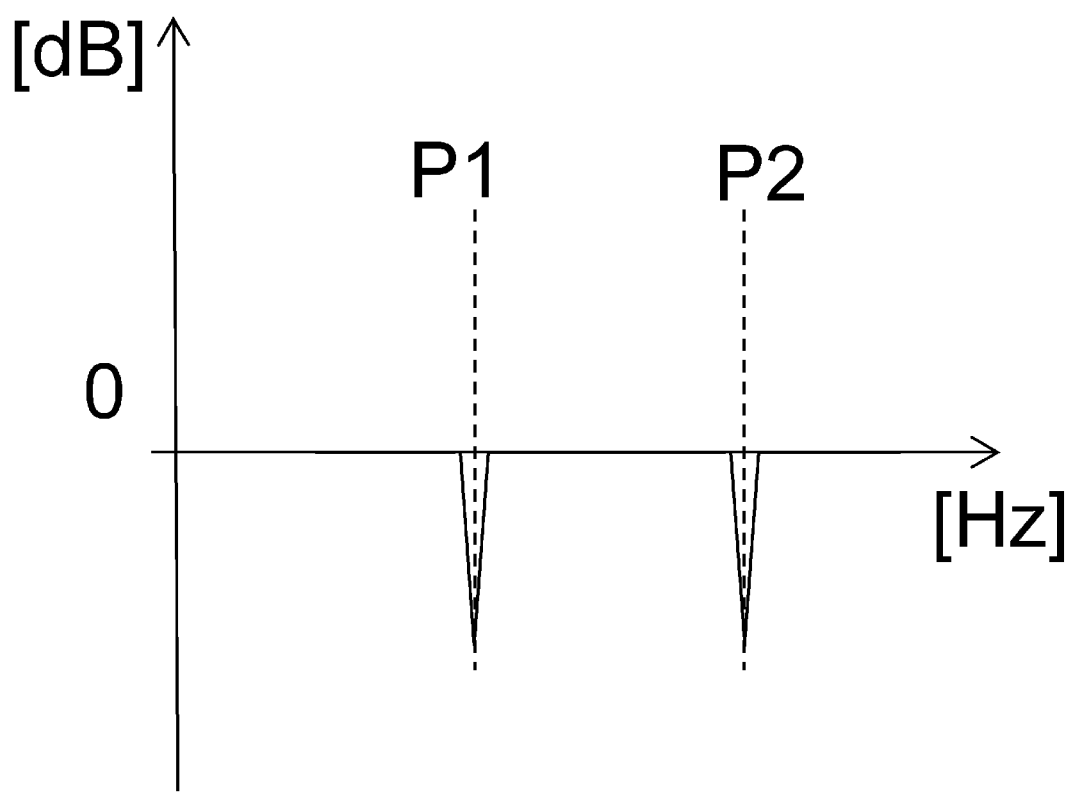
FIG. 6 shows a frequency response curve of the notch filter 37.
Figure 7:
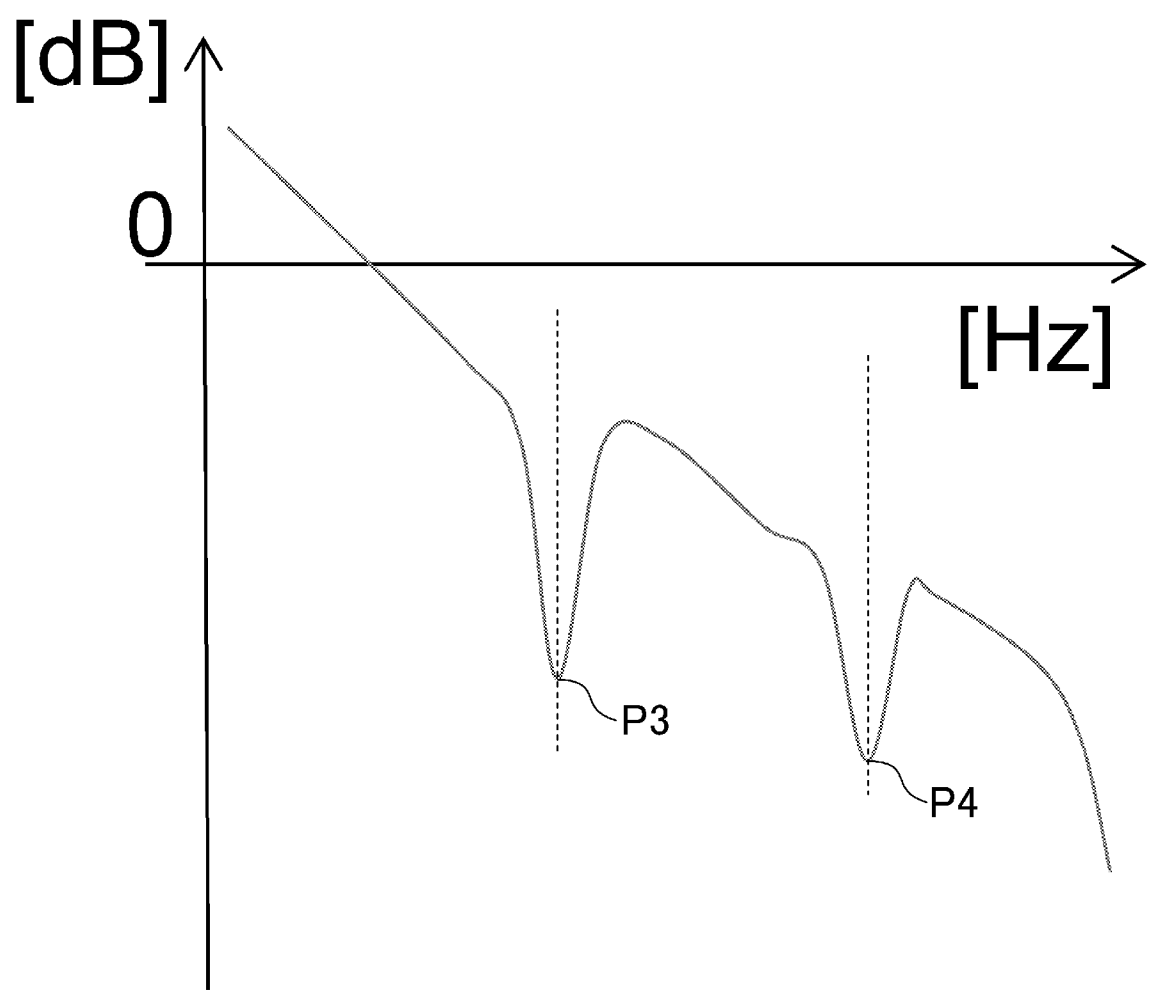
FIG. 7 shows a vibration frequency response curve of the control system loop with the notch filter 37.
Figure 8:
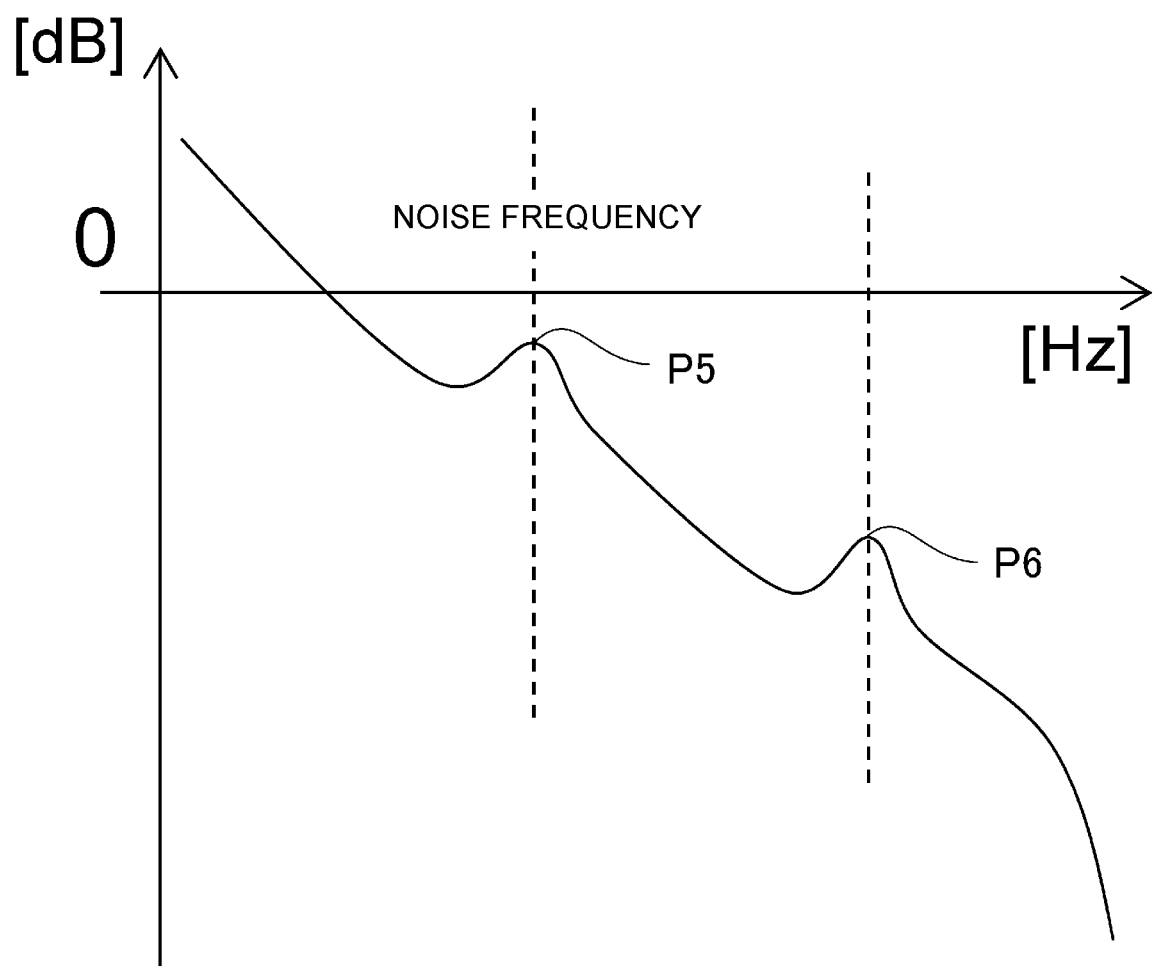
FIG. 8 shows a noise frequency response curve of the control system loop without the notch filter 37.
Figure 9:
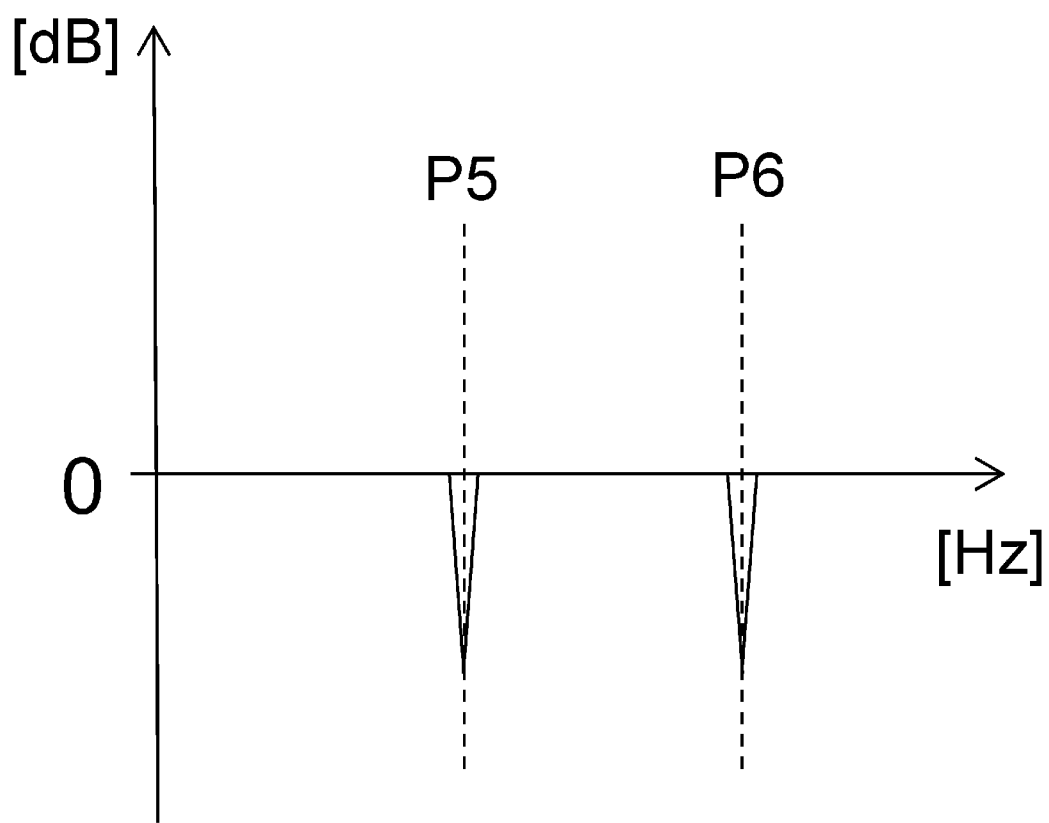
FIG. 9 shows a frequency response curve of the notch filter 37.
Figure 10:
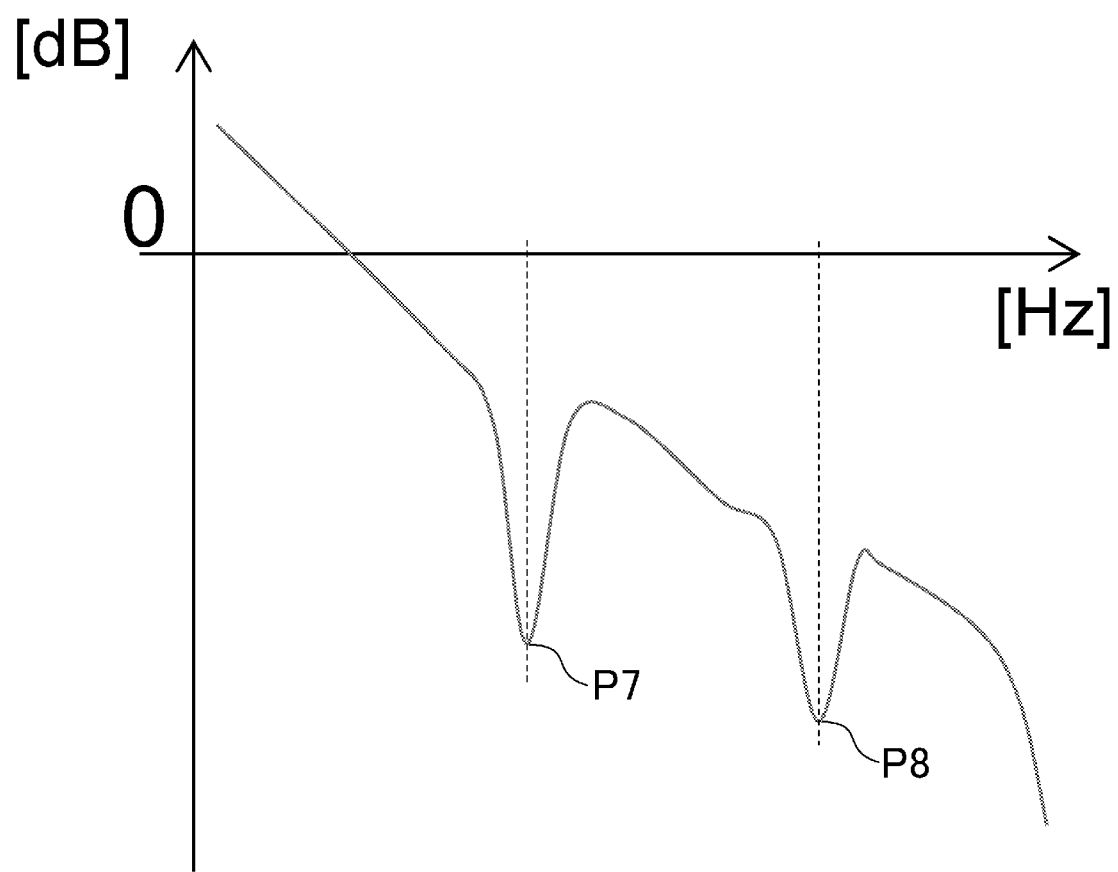
FIG. 10 shows a noise frequency response curve of the control system loop with the notch filter 37.

FIG. 4 is a block diagram of the blowing apparatus 100 illustrated in FIG. 1. FIG. 5 shows a vibration frequency response curve of a control system loop without a notch filter 37. FIG. 6 shows a frequency response curve of the notch filter 37. FIG. 7 shows a vibration frequency response curve of the control system loop with the notch filter 37. FIG. 8 shows a noise frequency response curve of the control system loop without the notch filter 37. FIG. 9 shows a frequency response curve of the notch filter 37. FIG. 10 shows a noise frequency response curve of the control system loop with the notch filter 37.

As illustrated in FIG. 4, the blowing apparatus 100 includes the sensor 129, a display unit 81, an operation unit 82, a control circuit 30, a driving circuit 21, the motor 125, the sound absorbing speaker 140, and the microphone 141. The motor 125 includes a Hall sensor 11 therein.

The sensor 129, the display unit 81, the operation unit 82, the control circuit 30, and the driving circuit 21 are mounted on the first circuit board 131. The sound absorbing speaker 140 and the microphone 141 are mounted on the second circuit board 132. The second circuit board 132 is electrically connected by wires (not shown) to the first circuit board 131.

The display unit 81 includes a display screen 181 illustrated in FIG. 1. On the display screen 181, the display unit 81 displays, for example, the setting information of the blowing apparatus 100. For example, on the display screen 181, the display unit 81 displays an air pressure (setting pressure) applied to the airway of the patient U in accordance with an instruction from the control circuit 30.

As illustrated in FIG. 1, the operation unit 82 includes a plurality of operation keys 182 for receiving the operation input. The plurality of operation keys 182 include, for example, a power key and a pressure setting key. With the plurality of operation keys 182, for example, a healthcare worker sets an air pressure applied to the airway of the patient U.

The microphone 141 detects a first sound produced by the blowing unit 120, and outputs a first audio signal representing the first sound to the control circuit 30. The control circuit 30 generates a second audio signal representing a second sound having a phase opposite to that of the first sound detected by the microphone 141, and outputs the generated second audio signal to the sound absorbing speaker 140.

The sound absorbing speaker 140 processes the second audio signal, and produces the second sound having a phase opposite to that of the first sound detected by the microphone 141. The sound absorbing speaker 140 faces toward the intake hole 106. Therefore, with the sound absorbing speaker 140, the blowing apparatus 100 can cancel out the noise that leaks through the intake hole 106.

Since the exhaust hole 111 is connected to the mask M with the tube T interposed therebetween, very little noise leaks through the exhaust hole 111. Therefore, in the blowing apparatus 100, the sound absorbing speaker 140 is positioned in such a manner as to face only toward the intake hole 106.

The control circuit 30 includes a pressure detecting unit 42, a pressure indicating unit 31, a subtractor 32, a speed detecting unit 17, a speed indicating unit 34, a subtractor 35, a speed control unit 36, and the notch filter 37. The notch filter 37 corresponds to a filter circuit of the present disclosure.

The blowing apparatus 100 includes a pressure sensor 41 attached to the exhaust hole 111. The pressure detecting unit 42 detects a present air pressure from the output of the pressure sensor 41, and outputs a value representing the present air pressure to the subtractor 32. On the other hand, the pressure indicating unit 31 outputs a value representing an air pressure (prescribed pressure) which is pre-set, for example, in the operation unit 82 to the subtractor 32. The subtractor 32 subtracts the value representing the present air pressure from the value representing the pre-set air pressure (prescribed pressure), and outputs a deviation signal to the speed indicating unit 34.

That is, in accordance with the output of the pressure sensor 41, the control circuit 30 monitors the air pressure applied to the airway of the patient U and performs pressure control. The flow rate of air changes as the patient U breathes. Even in this case, the pressure control is performed to keep the air pressure applied to the airway of the patient U constant, and the speed indicating unit 34 generates a signal representing a target rotation speed Y of the motor 125.

The pressure control is performed such that the pre-set air pressure (prescribed pressure) is reached, and the target rotation speed Y of the motor 125 is set in the speed indicating unit 34. The rotation speed of the motor 125 corresponds to the number of the revolutions of the fan 121. The air pressure applied to the airway of the patient U depends on the number of the revolutions of the fan 121.

That is, as the number of the revolutions of the fan 121 increases, the air pressure applied to the airway of the patient U increases. By lowering the pressure by a predetermined amount when the patient U breathes out, the speed indicating unit 34 can reduce the strain on the patient U.

Then, the speed indicating unit 34 outputs the signal representing the target rotation speed Y of the motor 125 to the subtractor 35.

The pressure sensor 41 may be positioned closer to the patient, rather than to the exhaust hole 111. For example, the pressure sensor 41 may be positioned in the tube T or mask M. This reduces the errors caused by the pressure loss or the like, and improves the accuracy of the pressure control.

The signal representing the target rotation speed Y of the motor 125 is supplied from the speed indicating unit 34 to the positive input of the subtractor 35. On the other hand, a signal representing a present rotation speed X of the motor 125 detected by the speed detecting unit 17 is supplied to the negative input of the subtractor 35. The subtractor 35 subtracts the signal representing the present rotation speed X of the motor 125 from the signal representing the target rotation speed Y, and outputs a deviation signal Y-X to the speed control unit 36.

The speed control unit 36 calculates a torque to be developed by the motor 125 such that the deviation signal Y-X is "0". Then, the speed control unit 36 outputs a torque command representing the calculated torque to the notch filter 37. In this case, for example, the speed control unit 36 multiplies the deviation signal Y-X by a gain to calculate a torque command based on the proportional control.

The notch filter 37 has a high attenuation effect on signals in a specific frequency band. For example, as shown in FIG. 5, the control circuit 30 pre-sets, in the notch filter 37, the frequencies corresponding to peaks P1 and P2 which are resonant frequencies unique to the blowing unit 120. The notch filter 37 thus has a frequency response such as that shown in FIG. 6. The notch filter 37 removes the frequency components corresponding to peaks P1 and P2 from the torque command received from the speed control unit 36.

Also, for example, as shown in FIG. 8, the control circuit 30 pre-sets, in the notch filter 37, the frequencies corresponding to peaks P5 and P6 of the frequency of the noise produced by the blowing unit 120. The fan 121 produces a vibration sound or noise, such as large wind noise, at a frequency corresponding to "(the rotation speed of the fan 121)×(the number of blades)" and an integral multiple of this frequency. The notch filter 37 thus has a frequency response such as that shown in FIG. 9. The notch filter 37 removes the frequency components corresponding to peaks P5 and P6 from the torque command received from the speed control unit 36.

Then, the notch filter 37 outputs the filtered torque command to the driving circuit 21.

Alternatively, the sensor 129 may detect the frequencies corresponding to peaks P1 and P2 which are resonant frequencies unique to the blowing unit 120, and the control circuit 30 may make setting of the notch filter 37 in accordance with the detection result outputted by the sensor 129. In this case, the blowing apparatus 100 can identify, with the sensor 129, the frequency of the vibration produced by the blowing unit 120 and set the identified frequency in the notch filter 37.

The driving circuit 21 converts the torque command passed through the notch filter 37 into a current value for developing the torque in the motor 125. Then, the driving circuit 21 supplies a driving current representing the resulting current value to the motor 125. The motor 125 is thus rotated by the torque. On the other hand, by the filtering process described above, the current values corresponding to peaks P1, P2, P5, and P6 are made substantially zero. Therefore, there is virtually no acceleration or deceleration of the motor 125 at the frequencies corresponding to peaks P1, P2, P5, and P6.

Next, the Hall sensor 11 detects a magnetic field generated inside the motor 125, and outputs an analog signal proportional to the magnitude of the magnetic field to the speed detecting unit 17. This analog signal represents the position of a rotor (not shown) included in the motor 125. In accordance with the analog signal received from the Hall sensor 11, the speed detecting unit 17 detects the present rotation speed X of the motor 125. Then, the speed detecting unit 17 outputs a detection signal representing the present rotation speed X of the motor 125 to the subtractor 35 in the same manner as above. That is, the present rotation speed X of the motor 125 is fed back to the subtractor 35.

By the feedback control described above, the rotation of the motor 125 is controlled until the target rotation speed Y is reached. At this point, the notch filter 37 removes the resonant frequencies and the noise frequencies of the blowing unit 120 from the torque command for drive-controlling the motor 125.

Thus, for example, as shown in FIGS. 5 and 7, the frequency signals representing peaks P1 and P2 are attenuated by the notch filter 37 and become frequency signals representing peaks P3 and P4. The blowing apparatus 100 can thus suppress the occurrence of the resonant vibration of the blowing unit 120.

Additionally, for example, as shown in FIGS. 8 and 10, the frequency signals representing peaks P5 and P6 are attenuated by the notch filter 37 and become frequency signals representing peaks P7 and P8. The blowing apparatus 100 can thus suppress the occurrence of the noise from the blowing unit 120.

In the blowing apparatus 100, the fan 121 includes the blades 123 that extend radially with respect to the rotation axis R. The diameter of the fan 121 is greater than the thickness of the fan 121. That is, the area of the upper surface of the fan 121 is greater than the area of the side face of the fan 121.

In the blowing apparatus 100, the first circuit board 131 intersects the rotation axis R of the fan 121 and covers the blowing unit 120. That is, in the blowing apparatus 100, the side face of the blowing unit 120 is covered with the middle casing 110 (single layer), and the upper surface of the blowing unit 120 is covered with the first circuit board 131 and the top casing 115 (multiple layers). This enables the blowing apparatus 100 to significantly attenuate the noise and vibration transmitted from the upper surface of the blowing unit 120 having a large area. At the same time, this allows the blowing apparatus 100 to be lightweight, because the side face of the blowing unit 120 having a small area is not covered with multiple layers.

The blowing apparatus 100 can thus significantly attenuate the noise and vibration produced by the blowing unit 120 without a significant increase in weight.

Additionally, in the blowing apparatus 100, the lower surface of the blowing unit 120 is covered with multiple layers, the second circuit board 132 and the bottom casing 105. This enables the blowing apparatus 100 to significantly attenuate the noise and vibration transmitted from the lower surface of the blowing unit 120 having a large area.

As illustrated in FIGS. 2 and 3, the exhaust hole 111 is located outside the perimeter of the plurality of blades 123 with respect to the rotation axis R. The diameter of the exhaust hole 111 is greater than the length of the blades 123 in a direction parallel to the rotation axis. During rotation of the fan 121, air from the perimeter of the fan 121 is discharged through the exhaust hole 111 to the outside of the casing. Thus, the air from the fan 121 can easily reach the exhaust hole 111 directly without much hitting other components. The blowing apparatus 100 can thus efficiently discharge air through the exhaust hole 111. Also, the blowing apparatus 100 can achieve a silencing effect, since air is less likely to hit other components.

Other Embodiments

Although the foregoing embodiment uses air as a gas, the present disclosure is not limited to this. The present disclosure is applicable even when the gas is a mixture of air and oxygen in practice.

In the foregoing embodiment, the first circuit board 131 overlaps the entire blowing unit 120 as viewed from the top casing 115 in a plan view of the first circuit board 131. However, the present disclosure is not limited to this. In practice, the first circuit board 131 may overlap with only a part of the blowing unit 120 as viewed from the top casing 115 in a plan view of the first circuit board 131.

Although the blowing apparatus is used for continuous positive airway pressure (CPAP) in the foregoing embodiment, the present disclosure is not limited to this. In practice, the blowing apparatus may be used for other applications, such as mechanical artificial respiration.

Although the motor 125 includes the Hall sensor 11 in the foregoing embodiment, the present disclosure is not limited to this. In practice, the motor 125 may include at least one of the Hall sensor 11 and an encoder. The encoder outputs a rotation signal to the speed detecting unit 17 in accordance with the rotation angle position of the motor 125.

The foregoing description of the embodiments is to be considered illustrative, not restrictive, in all respects. The scope of the present disclosure is defined by the appended claims, not by the foregoing embodiments. The scope of the present disclosure includes scopes equivalent to the appended claims.

M: mask
R: rotation axis
T: tube
U: patient
11: Hall sensor
17: speed detecting unit
21: driving circuit
30: control circuit
31: pressure indicating unit
32: subtractor
34: speed indicating unit
35: subtractor
36: speed control unit
37: notch filter
41: pressure sensor
42: pressure detecting unit
81: display unit
82: operation unit
100: blowing apparatus
105: bottom casing
106: intake hole
110: middle casing
111: exhaust hole
112: nozzle
115: top casing
116: securing portion
120: blowing unit
121: fan
123: blade
124: mounting plate
125: motor
129: sensor
131: first circuit board
132: second circuit board
140: sound absorbing speaker
141: microphone
181: display screen
182: operation key

The invention claimed is:

1. A blowing apparatus comprising:
a blowing unit including a fan and a motor configured to rotate the fan;
a first circuit board having a control circuit mounted thereon, the control circuit being configured to control drive of the motor, the first circuit board intersecting a rotation axis of the fan; and
a casing having an intake hole and an exhaust hole, the casing housing the blowing unit and the first circuit board; and
a second circuit board intersecting the rotation axis of the fan and housed in the casing,
wherein the first circuit board overlaps with the blowing unit in a plan view of the first circuit board, and wherein the second circuit board is located under the blowing unit, and overlaps with a whole area of the blowing unit in a plan view of the second circuit board.

2. The blowing apparatus according to claim 1, wherein the blowing unit is located in a region between the first circuit board and the second circuit board.

3. The blowing apparatus according to claim 2, wherein the casing has a securing portion configured to secure the first circuit board; and
the first circuit board and the securing portion are bonded together with an elastic member interposed between the first circuit board and the securing portion.

4. The blowing apparatus according to claim 2, wherein the control circuit includes a filter circuit configured to attenuate signals in a specific band.

5. The blowing apparatus according to claim 2, further comprising:
a microphone configured to detect a first sound produced by the blowing unit; and
a sound absorbing speaker configured to produce a second sound having a phase opposite to a phase of the first sound detected by the microphone,
wherein the sound absorbing speaker is housed in the casing while facing toward the intake hole.

6. The blowing apparatus according to claim 1, wherein the casing has a securing portion configured to secure the first circuit board; and
the first circuit board and the securing portion are bonded together with an elastic member interposed between the first circuit board and the securing portion.

7. The blowing apparatus according to claim 6, wherein the control circuit includes a filter circuit configured to attenuate signals in a specific band.

8. The blowing apparatus according to claim 1, wherein the control circuit includes a filter circuit configured to attenuate signals in a specific band.

9. The blowing apparatus according to claim 8, further comprising a sensor configured to detect a frequency of sound or vibration produced by the drive of the motor,
wherein the control circuit is configured to set the specific band to be attenuated by the filter circuit based on a detection result outputted by the sensor.

10. The blowing apparatus according to claim 1, further comprising:
a microphone configured to detect a first sound produced by the blowing unit; and
a sound absorbing speaker configured to produce a second sound having a phase opposite to a phase of the first sound detected by the microphone,
wherein the sound absorbing speaker is housed in the casing while facing toward the intake hole.

11. The blowing apparatus according to claim 1, wherein the fan includes a plurality of blades extending radially with respect to the rotation axis;
the exhaust hole is located outside a perimeter of the plurality of blades with respect to the rotation axis; and
a diameter of the exhaust hole is greater than a length of each of the blades in a direction parallel to the rotation axis.

12. The blowing apparatus according to claim 1, wherein the first circuit board overlaps with a whole area of the blowing unit in a plan view of the first circuit board, and the first circuit board is located above the fan.

13. The blowing apparatus according to claim 1, wherein the motor is located between the fan and the first circuit board.

* * * * *